US011653900B2

(12) United States Patent
Toporek et al.

(10) Patent No.: US 11,653,900 B2
(45) Date of Patent: May 23, 2023

(54) DATA AUGMENTATION FOR TRAINING DEEP LEARNING MODELS WITH ULTRASOUND IMAGES

(71) Applicant: KONINKLIJKE PHILIPS N.V., Eindhoven (NL)

(72) Inventors: Grzegorz Andrzej Toporek, Cambridge, MA (US); Jun Seob Shin, Cambridge, MA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 365 days.

(21) Appl. No.: 16/839,420

(22) Filed: Apr. 3, 2020

(65) Prior Publication Data
US 2020/0315587 A1 Oct. 8, 2020

Related U.S. Application Data

(60) Provisional application No. 62/829,316, filed on Apr. 4, 2019.

(51) Int. Cl.
*G06N 3/08* (2023.01)
*G06T 19/00* (2011.01)
(Continued)

(52) U.S. Cl.
CPC ............ *A61B 8/5207* (2013.01); *A61B 8/488* (2013.01); *A61B 8/5246* (2013.01); *G06N 3/08* (2013.01);
(Continued)

(58) Field of Classification Search
CPC ..... A61B 8/5207; A61B 8/488; A61B 8/5246; A61B 8/08; A61B 8/14; A61B 8/483;
(Continued)

(56) References Cited

U.S. PATENT DOCUMENTS

2014/0177947 A1 6/2014 Hinton et al.
2018/0018757 A1* 1/2018 Suzuki ................. G06T 3/4053
(Continued)

FOREIGN PATENT DOCUMENTS

| CN | 107748900 A | * | 3/2018 | ........... G06K 9/3233 |
| WO | WO-2009106784 A1 | * | 9/2009 | ............... A61B 8/58 |
| WO | WO-2018011631 A2 | * | 1/2018 | ........... A61B 6/5217 |

OTHER PUBLICATIONS

Bell, M. Improved endocardial border definition with short-lag spatial coherence (SLSC) imaging. PhD Dissertation, Duke University 2012.
(Continued)

*Primary Examiner* — Grace Q Li

(57) ABSTRACT

Various embodiments relate to a method for managing healthcare resources including receiving information selecting a first outcome perspective, calculating first impactibility scores for the first outcome perspective, determining a first subarea based on the first impactibility scores, and designating an allocation of healthcare resources and cost for the first subarea based on the first outcome perspective. The first impactibility scores are calculated for respective subareas including the first subarea, and the first outcome perspective corresponds to a first ratio of healthcare resources and cost.

15 Claims, 7 Drawing Sheets

(51) Int. Cl.
  *G06V 20/20* (2022.01)
  *A61B 8/08* (2006.01)
  *G06N 20/00* (2019.01)
  *G16H 30/40* (2018.01)

(52) U.S. Cl.
  CPC ............ *G06N 20/00* (2019.01); *G06T 19/006* (2013.01); *G06V 20/20* (2022.01); *G16H 30/40* (2018.01)

(58) Field of Classification Search
  CPC ........ A61B 8/485; A61B 8/5269; G06N 3/08; G06N 20/00; G06N 3/0454; G06N 7/005; G06T 19/006; G06V 20/20; G16H 30/40; G16H 50/70
  See application file for complete search history.

(56) References Cited

U.S. PATENT DOCUMENTS

2019/0328368 A1\* 10/2019 Pedersen .............. A61B 8/5269
2020/0160978 A1\* 5/2020 Prosky ................... G16H 15/00

OTHER PUBLICATIONS

Goodfellow, I. et al., "Deep Learning". MIT Pressbook. Table of Contents, Year: 2016.

\* cited by examiner

DATA AUGMENTATION FOR TRAINING DEEP LEARNING MODELS WITH ULTRASOUND IMAGES

TECHNICAL FIELD

This disclosure relates generally to data augmentation for training deep learning models with ultrasound images.

BACKGROUND

Training a particularly complex neural network (i.e., a network having a large number of parameters) may lead to overfitting. Overfitting occurs when the neural network simply memorizes provided training data, rather than generalizes well to new examples. Overfitting may be overcome by providing more training data. However, collection of data for large labelled clinical cases is either not feasible or laborious and expensive.

Another reason for poor generalizations of deep learning type algorithms is an existing bias in the training dataset. For instance, training cases including labelled ultrasound images may be biased against certain patient population subgroups, such as only healthy or non-obese patients. In obese patients, for example, image quality may be inferior due to strong reverberation and aberration artefacts thus leading to significant prediction inaccuracies of neural networks trained using such patient images.

SUMMARY

A brief summary of various example embodiments is presented. Some simplifications and omissions may be made in the following summary, which is intended to highlight and introduce some aspects of the various example embodiments, but not to limit the scope of the invention.

Detailed descriptions of example embodiments adequate to allow those of ordinary skill in the art to make and use the inventive concepts will follow in later sections.

Various embodiments relate to a method for generating an augmented training set of ultrasound images, including: randomly selecting one ultrasound image from a labeled set of ultrasound images; randomly selecting one of a set of ultrasound augmentation models; combining the randomly selected ultrasound image and randomly selected ultrasound augmentation model to produce an augmented ultrasound image; and training a machine learning model using the augmented ultrasound image.

Various embodiments are described, wherein combining the randomly selected ultrasound image and randomly selected ultrasound augmentation model includes using one of a weight-based image blending, Laplacian pyramid blending, selective, region-based blending, two-band blending, and graph-cuts based blending.

Various embodiments are described, wherein a parameter of the blending is randomly chosen.

Various embodiments are described, wherein the machine learning model is a convolutional neural network model.

Various embodiments are described, wherein the ultrasound augmentation model is one of a reverberation artefacts model, comet tail artefacts model, shadowing artefacts model, near-field clutter model, range ambiguity model, beam-width artefact model, refraction model, and aberration model.

Various embodiments are described, wherein the ultrasound augmentation model is one depth of focus of the ultrasound image alteration, time gain control (TGC) curve alteration, gain alteration, quadrature bandpass (QBP) filter and weights alteration, XRES settings alteration, and autoscan settings alteration.

Various embodiments are described, wherein the machine learning model performs one of the following tasks: classification; segmentation; detection; regression; data generation; view identification; and text generation.

Various embodiments are described, wherein the ultrasound image is one of a color Doppler image, three-dimensional volumetric image, B-mode image, raw radiofrequency data image, pre-scan converted image, scan converted image, and elastography image.

Further various embodiments relate to an ultrasound image augmentation training system, including: a machine learning model; an ultrasound image dataset including labeled ultrasound images; an augmentation controller configured to: randomly select one of the labeled of ultrasound images from the ultrasound image dataset; randomly select one of a set of ultrasound augmentation models; and combine the randomly selected ultrasound image and randomly selected ultrasound augmentation model to produce an augmented ultrasound image; and a training controller configured to train a machine learning model using the augmented ultrasound image.

Various embodiments are described, wherein combining the randomly selected ultrasound image and randomly selected ultrasound augmentation model includes using one of a weight-based image blending, Laplacian pyramid blending, selective, region-based blending, two-band blending, and graph-cuts based blending.

Various embodiments are described, wherein a parameter of the blending is randomly chosen.

Various embodiments are described, wherein the machine learning model is a neural network model.

Various embodiments are described, wherein the ultrasound augmentation model is one of a reverberation artefacts model, comet tail artefacts model, shadowing artefacts model, near-field clutter model, range ambiguity model, beam-width artefact model, refraction model, and aberration model.

Various embodiments are described, wherein the ultrasound augmentation model is one depth of focus of the ultrasound image alteration, time gain control (TGC) curve alteration, gain alteration, quadrature bandpass (QBP) filter and weights alteration, XRES settings alteration, and autoscan settings alteration.

Various embodiments are described, wherein the machine learning model performs one of the following tasks: multi-class classification; segmentation; detection; regression; and text generation.

Various embodiments are described, wherein the ultrasound image is one of a color Doppler image, three-dimensional volumetric image, B-mode image, raw radiofrequency data image, pre-scan converted image, scan converted image, and elastography image.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate example embodiments of concepts found in the claims and explain various principles and advantages of those embodiments.

These and other more detailed and specific features are more fully disclosed in the following specification, reference being had to the accompanying drawings, in which.

DETAILED DESCRIPTION

Figure 1:
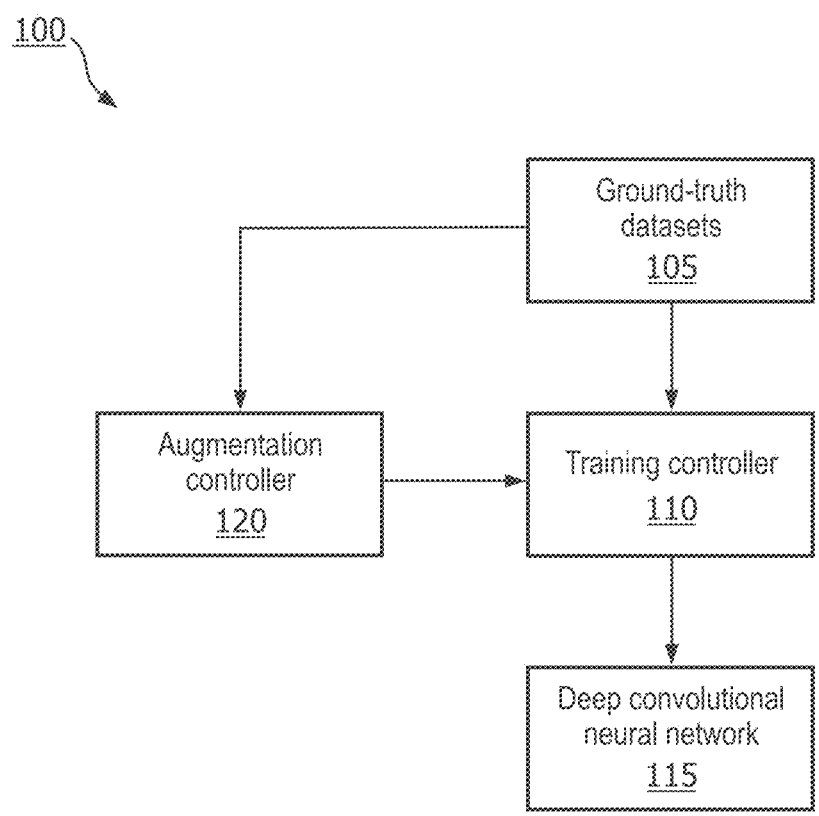
FIG. 1 illustrates a block diagram of an augmentation system.

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. Descriptors such as "first," "second," "third," etc., are not meant to limit the order of elements discussed, are used to distinguish one element from the next, and are generally interchangeable.

Figure 3A:
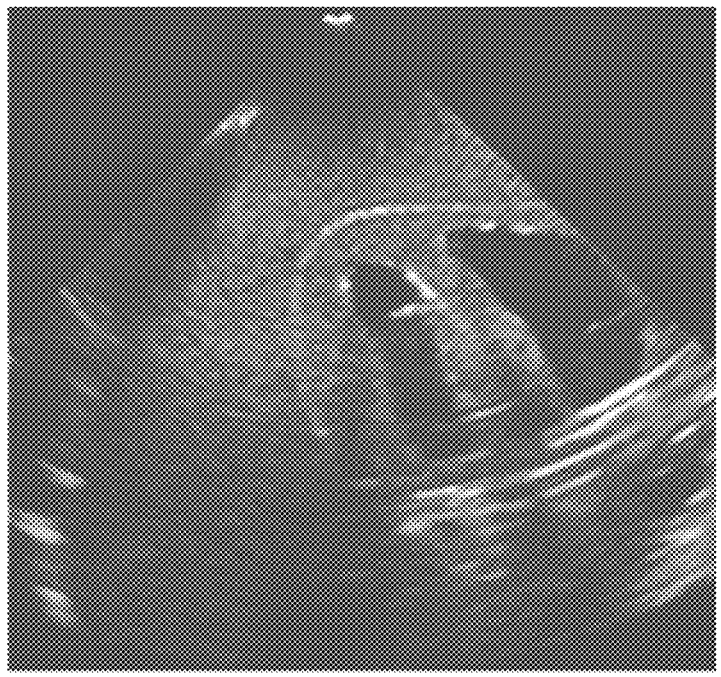
FIG. 3A illustrates cardiac ultrasound images with no reverberation clutter.
Figure 3B:
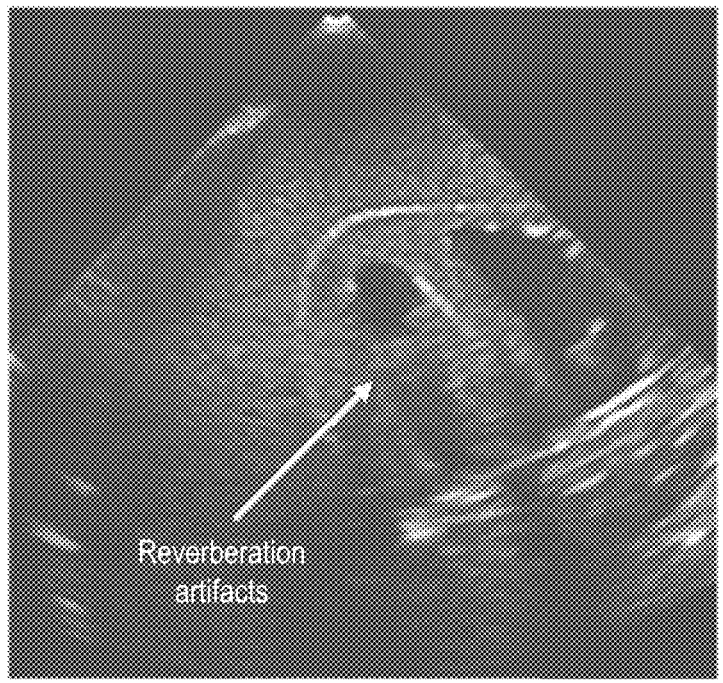
FIG. 3B illustrates cardiac ultrasound images with reverberation clutter.

As discussed above, in obese patient's image quality may be inferior due to strong reverberation and aberration artefacts, thus leading to significant prediction inaccuracies of neural networks. FIGS. 3A and 3B illustrate two cardiac phantom ultrasound images. The first image in FIG. 3A has no reverberation clutter, and the second image in FIG. 3B includes reverberation clutter. The reverberation clutter makes it more difficult recognize and identify various features of the heart.

Data augmentation has been developed to help expand the available training sets to improve the training of deep learning neural networks and other machine learning models. Data augmentation includes a synthetic creation of new training cases based on an existing training dataset. Data augmentation is also a type of regularization method in the field of deep learning that reduces generalization error but not its training error. In one example of a system for generation of training cases given an initial set of cases includes using a color-space deformation.

Embodiments of a data augmentation system using training cases including ultrasound images is described herein. This data augmentation system may be used as a regularization technique for training neural networks on various tasks involving ultrasound data, such as: breast tumor classification (malignant vs. benign); ultrasound imaging plane adjustment (pose regression); liver tumor or vessel segmentation; view classification (e.g. parasternal vs. apical imaging window); image quality or similarity assessment (good vs. low-quality frame); object detection and localization (e.g. detection of fetal femur in obstetric ultrasound); deep learning-based ultrasound image generation and artifact removal (e.g. using generative adversarial network [GAN]), etc. Starting with an initial set of labelled ground-truth ultrasound images, the data augmentation system injects one of a previously acquired artefact models, such as a reverberation signal model, and matches the synthesized cases with the previously provided labels from the ground-truth ultrasound images.

Data-driven deep learning type algorithms require a large number of training cases in order to generalize to a specific task. Collection of large training datasets of labeled (i.e., where a specific diagnosis or condition is associated with the image) medical ultrasound images is very laborious and therefore expensive. A typical regularization technique used during training is data augmentation. Most of the available data augmentation methods, including shear, translation, rotation, zooming, changing of viewpoint and illumination, which are used for natural RGB images, are not suitable or robust enough for ultrasound images. Ultrasound images may contain various artefacts, such as comet tail, speckle, acoustic shadowing, or reverberation artefacts. These artefacts need to be accounted for and are very different than the standard shear, translation, rotation, zooming, changing of viewpoint and illumination techniques used with natural RGB images.

For instance, reverberation artefacts are typically present on ultrasound images acquired from patients with narrow intercostal spaces or large content of subcutaneous fat. These artefacts may significantly influence prediction accuracy of neural networks. Thus, being able to augment ultrasound images by adding different reverberation levels to a set of ground-truth images allows for the deep learning model to be trained to deal with a wider variety reverberation levels, and thereby improves the overall accuracy of the model.

Embodiments of a system for data augmentation of training cases including ultrasound images, such as color Doppler, B-mode, 3D ultrasound images as well as raw radiofrequency (RF) data will now be described.

FIG. 1 illustrates a block diagram of an augmentation system 100. The augmentation system 100 includes ground-truth datasets 105, a training controller 110, a deep convolutional neural network 115, and an augmentation controller 120.

The ground-truth datasets, which may be stored on a data storage device that is part of the augmentation system, may include a training case u labelled with the information in, for example, one of the following formats:

Benign (0), malignant (1) labels for binary classification;
Binary mask of the anatomical structure/lesion for segmentation tasks, where anatomical structure/lesion is represented by 1 and background by 0;

Bounding box around the anatomical structure/lesion for detection task; and

Position of the transducer with respect to some reference coordinate system for pose regression tasks.

And many others (e.g. ground truth for image generation, view classification . . . )

Further, the ground-truth training cases may be collected and stored in different formats, including, for example:

Raw radiofrequency (RF) data;
Pre-scan converted data;
Scan converted data;
Elastography ultrasound images;
Color Doppler ultrasound images;
B-mode images; and
3D volumetric images.

If the data is in a Cartesian format, then it is converted to a polar format. It is noted the raw radiofrequency (RF) data is typically in a polar format. In this example, all augmentation is then performed in the polar domain followed by envelope detection, log-compression, and scan conversion on each augmented data case. The augmentation may be done in the Cartesian domain as well as other domains as needed. Also, if RF data is available, the RF data may be beamformed to generate images on the fly during the training process and use different beamforming methods as an augmentation technique.

The training controller 110 trains the deep neural network 115 using methods known in art, such as batchwise training, based on the data provided from the augmentation controller 120. The training data may include the various types of data described above that will have associated labels, for example benign/malignant or anatomical structure/lesion. This training data may be split, and part of the data used to train the model, and the remaining data used for validation of the model.

The deep convolutional neural network 115 is trained to perform a specific task using ultrasound data, such color Doppler, B-mode, 3D ultrasound images as well as raw radiofrequency (RF) data. For instance, the deep convolutional neural network 115 may predict the malignancy of a lesion given a breast ultrasound image. The deep convolutional neural network 115 typically has a number of layers, depending on the complexity of the task, which is specified in its last layer. All the intermediate layers are convolutional layers, including convolution, non-linear regularization, batch normalization and spatial pooling. The deep convolutional neural network 115 may be trained to perform various tasks including, for example, the following tasks:

Multi-class or binary classification (e.g., benign vs malignant lesion, . . . ;
Segmentation (e.g. segmentation of liver vasculature);
Detection (e.g. detection of certain anatomical structures, such as left ventricle);
Regression (e.g. pose regression—regression of the position of the image with respect to some anatomy); or
Text generation (e.g. creation of reports based on the input image or providing labels of certain identified features).

Figure 2:
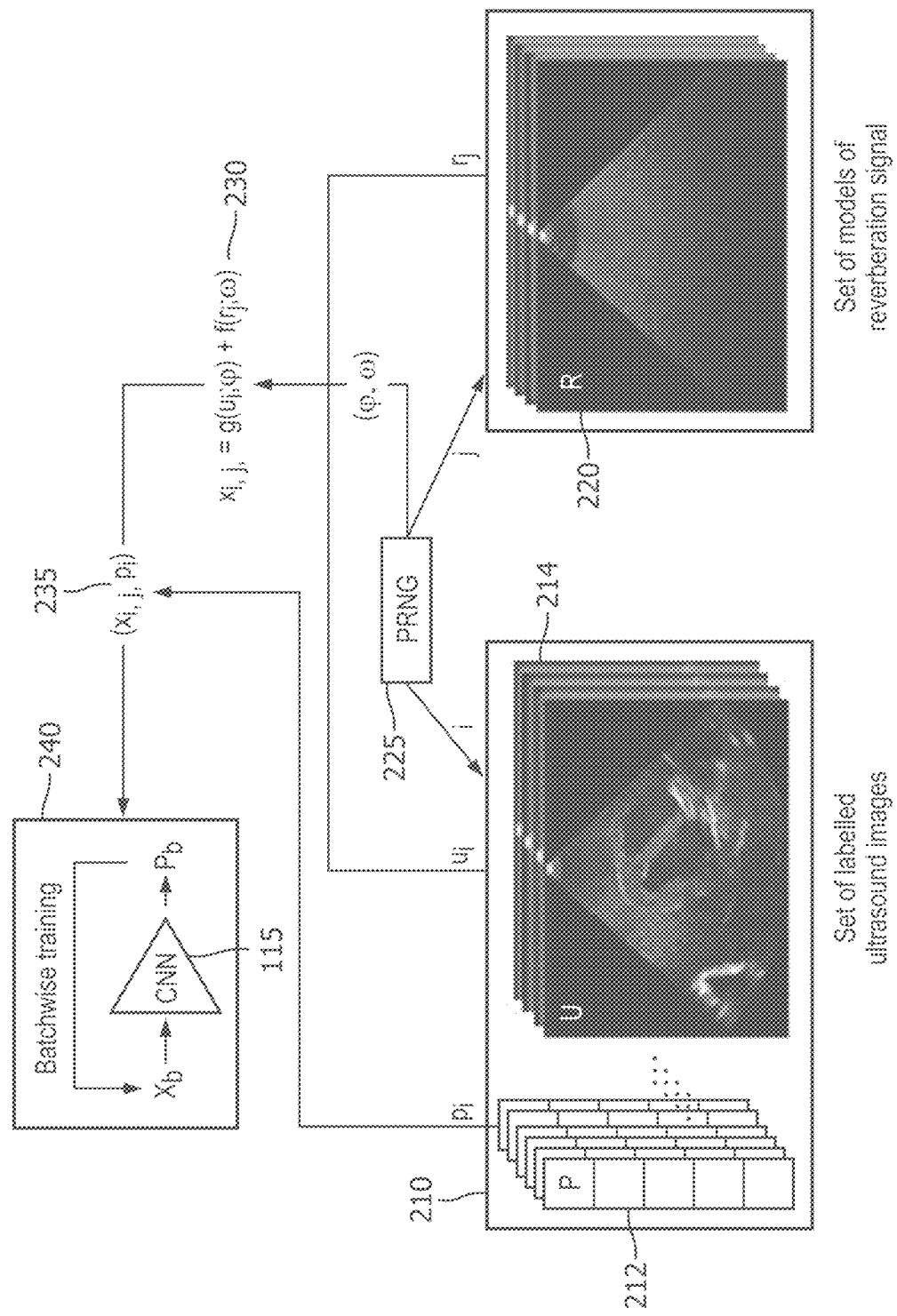
FIG. 2 illustrates how the augmentation controller trains the deep convolutional neural network model.

FIG. 2 illustrates how the augmentation controller 120 trains the deep convolutional neural network model 115. The pseudorandom number generator (PRNG) 225 randomly generates a number that is used to randomly choose a 2-tuple (u, p) from the ground-truth datasets (U, P) 210, where p is a label 212 for a training case u 214; for instance, u is an B-mode ultrasound image of a breast lesion 214, and p is a binary mask 212 on which the lesion is represented by 1 and the background by 0. Next, the augmentation controller 120 combines 230 the training case u from the selected 2-tuple with an artefact model using a weighted model. The PRNG 225 generates another random number to randomly select a specific artifact signal model r. Training case u and artefact model r may be combined using one or a combination of the following methods that are known in the art:

Weight-based image blending:
$x = \varphi u + \omega r$, where $\omega = 1 - \varphi$;
Laplacian pyramid blending;
Selective, region-based blending;
Two-band blending;
Graph-cuts based blending; or
Other segmentation based blending techniques.

It is noted that the blending of ultrasound image with the artefacts model, especially reverberation signal model, typically is performed in the polar domain.

In FIG. 2 a weighted model 230 is used where the random number generator randomly selects the values for co and cp.

Alternative ultrasound artefact models may include but are not limited to:

Comet tail artefacts;
Shadowing artefacts;
Near-field clutter;
Range ambiguity;
Beam-width artefact;
Refraction; or
Aberration.

Alternative image alteration methods for ultrasound data augmentation may include but are not limited to:

alteration of the depth, that is the depth of focus of the image;
alteration of the Time Gain Control (TGC) curve;
alteration of gain;
alteration of quadrature bandpass (QBP) filters and their weights for frequency compounding if RF data is available;
XRES on/off and/or alteration of XRES settings, where XRES adaptively enhances ultrasound images by reducing speck, improving contract etc.; or
Autoscan on/off, where autoscan automatically optimizes gain and TGC continuously in real-time to provide optimal images.

The augmentation system 100 may generate the reverberation signal modes as follows. First, a set R of r reverberation signal models are a priori created using methods known in the literature (see for example, Bell, M. Improved endocardial border definition with short-lag spatial coherence (SLSC) imaging. *PhD Dissertation, Duke University* 2012)). The model of a reverberation signal may be, for instance, created using metal sponge attached to the transducer and immerged into the water tank, and the reverberation signal is then stored on a storage media in the following format: $R = \{r_1, r_2, \ldots, r_m\}$. FIG. 3A illustrates a cardiac ultrasound image without reverberation artifacts. FIG. 3B illustrates the same cardiac ultrasound image with reverberation artifacts caused by the use of a metal sponge between the ultrasound transducer and the patient. At least one reverberation artifact is noted in FIG. 3B.

Next, the augmentation system 100 collects an initial training dataset U including u ultrasound training cases 214, and where the collected training data set is automatically or manually labelled by expert users with vectors p 212 based upon the conditions or features identified in the ultrasound images. The labeled data set is then stored on the storage media as a 2-tuples (u,p) 210 as follows:

$$(U,P) = \{(u_1, p_1)_1, (u_2, p_2)_2, \ldots, (u_n, p_n)_n\}.$$

Next, the augmentation system uses one of the available image post-processing techniques known in the art, such as those listed below, to augment training cases:

weight-based blending may be used as follows:

$$x = \varphi u + \omega r, \text{ where } \omega = 1 - \varphi;$$

alteration of the depth (example give below); and alteration of the TGC curve (example give below).

Figure 4A:
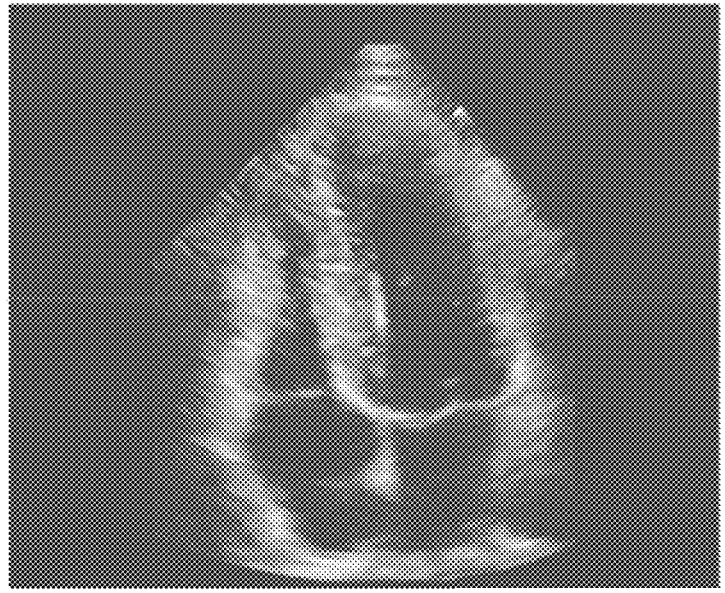
FIG. 4A illustrates a transthoracic echocardiography image (apical four chamber view)
Figure 4B:
FIG. 4B illustrates an augmented version of the image in FIG. 4A using a reverberation model and a weight-based blending of the original image and the reverberation model.

FIG. 4A illustrates a transthoracic echocardiography image (apical four-chamber view). FIG. 4B illustrates an augmented version of the image in FIG. 4A using a reverberation model and a weight-based blending of the original image and the reverberation model.

It is noted that on current ultrasound machines, post processing options may also include adjustments to primary adjustments such as gain, TGC, color doppler gain, pulsed wave (PW) doppler gain, continuous wave (CW) doppler gain, dynamic range and compression. However, these adjustments do not have the same effect as when the image is live.

Then, the augmented 2-tupes (x, p) 235 are sent to the training controller 110 that runs a batchwise training 240 of the deep convolutional neural network (CNN) 115. The training process may have many iterations. At each iteration a generated batch $(X_b, P_b)$, which includes m randomly selected 2-tuples is fed into a CNN with a predetermined structure, i.e., the number of input features, the number and types of layers, and the desired output. The network accepts the site set $X_b$ at its input layer and transfers the ground truth set $P_b$ to its output layer directly. The network is full of need-to-be-learned weights. At each iteration of the learning process, these weights are constantly updated by propagating the errors between the predicted transformation and the ground truth, first in a backward direction and then in a forward direction. Training of the weights will not be stopped until the transformation predicted from the network is similar enough to the ground truth, as for instance defined by the early stopping regularization technique that is known in the art.

Figure 5A:
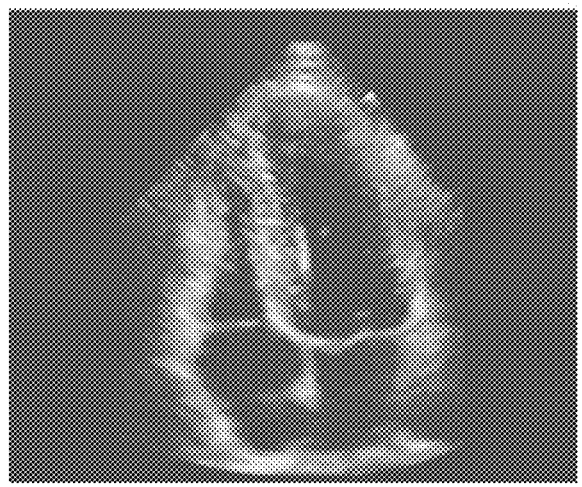
FIG. 5A illustrates the original input ultrasound image.
Figure 5B:
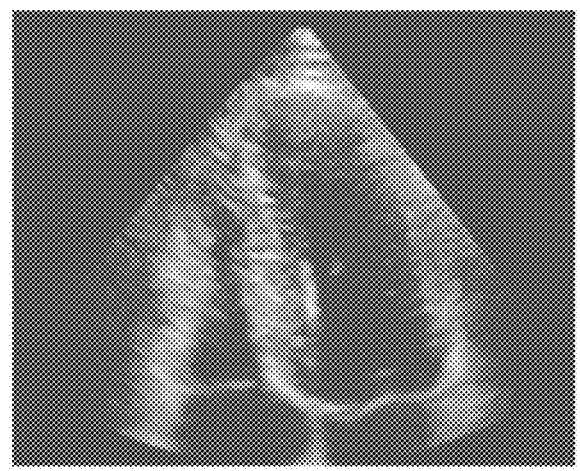
FIGS. 5B and 5C show two augmented images with reduced penetration depth.
Figure 5C:

Now two further embodiments of using the augmentation system will be discussed. In the second embodiment ultrasound images may be augmented by alternating the ultrasound image depth using image post-processing. FIG. 5A illustrates the original input ultrasound image. FIGS. 5B and 5C show two augmented images with reduced penetration depth. To alternate depth of the scan converted ultrasound image, the original image is first converted back from Cartesian to polar coordinate system. Then image samples are eliminated from the bottom of the image such that a predetermined image depth that is shorter than the initial image depth is achieved. Finally, the image is converted back to the Cartesian space via scan conversion methods known in the art. This results in the augmented images such as those in FIGS. 5B and 5C.

In a third embodiment, during image acquisition the sonographer may modify the TGC curve to improve the image quality by compensating for depth, which normalizes signal amplitude with time. In this embodiment the ultrasound images are augmented by applying a linear transformation along the vertical direction of the image (depth) in order to synthesize ultrasound images with various TGC curves.

Figure 6A:
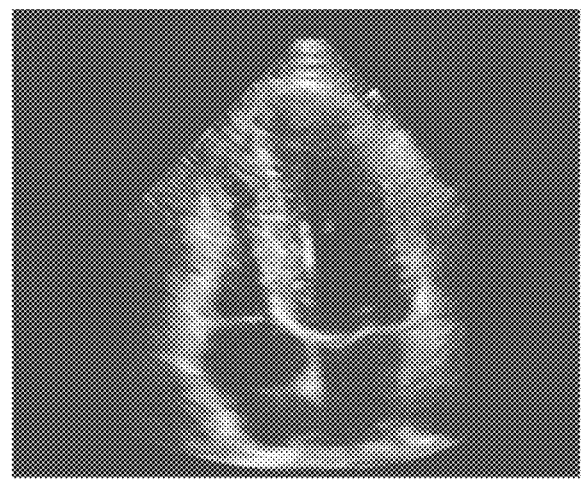
FIG. 6A is an example ultrasound image.
Figure 6B:
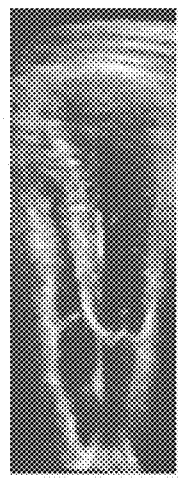
FIG. 6B is the ultrasound image of FIG. 6A converted to polar coordinates.
Figure 6C:
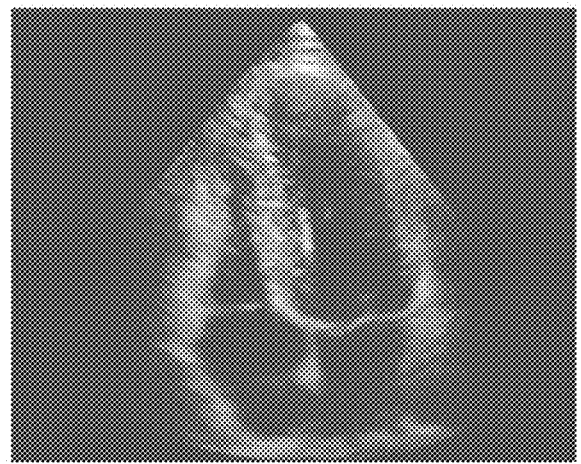
FIG. 6C, FIG. 6D, and FIG. 6E each show augmented images where $\theta=0.6$, $\theta=0.2$, and $\theta=-0.6$ respectively.
Figure 6D:
Figure 6E:
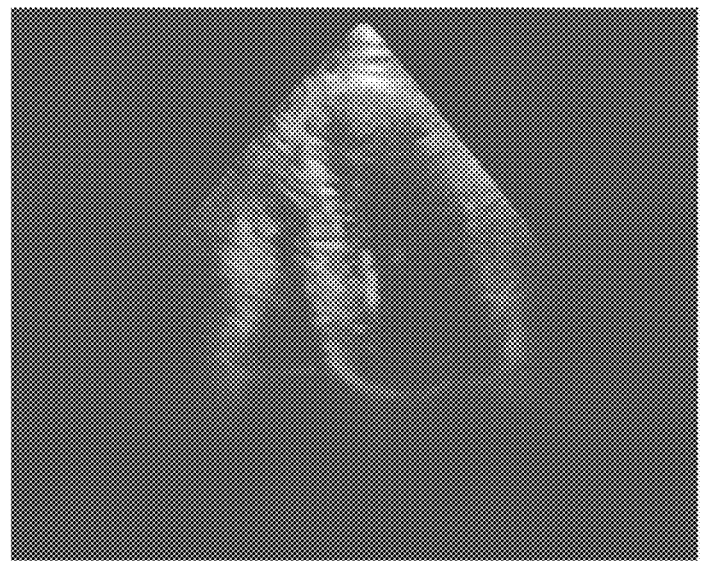

An original ultrasound image as shown in FIG. 6A is converted from the Cartesian to the polar coordinate system $p_u$ using methods known in the art resulting in the image as shown in FIG. 6B. If the input data is stored as polar data, the conversion from Cartesian to polar is unnecessary. All augmentation is then performed in the polar domain followed by envelope detection, log-compression, and scan conversion on each augmented data case. A linear transformation function is applied to each pixel of the input image as listed by the equation:

$$p_x(i,j) = (\arctan 2(1-\theta,h)(h-j)+\theta) \cdot p_u(i,j)$$

$$\forall \in \{0 \ldots w-1\}$$

$$\forall_j \in \{0 \ldots h-1\},$$

where θ stands for a random number selected by the PRNG where parameter θ∈<−1,1>, h and w stand for height and width of the image in the polar space respectively, and i,j are the indices of the pixels in the polar space. Then the image $p_x$ is converted back to the Cartesian space x, and the image x is then associated with the label p and sent to the training controller. FIGS. 6C, 6D, and 6E each show augmented images where θ=0.6, θ=−0.2, and θ=−0.6 respectively.

In yet another embodiment, two or more different types of augmentation may be randomly selected and combined with a ground truth data image using random weights. This allows for the combination of effects that might be seen in real captured ultrasound images.

The augmentation system and methods described herein may be used to improve generalizability of deep convolutional neural networks that are trained on various tasks for a broad range of ultrasound applications, for example: breast cancer classification; liver lesion or vessels segmentation from abdominal ultrasound images; imaging place adjustment via pose regression from ultrasound images; or other type of classification methods, such as view identification, image quality assessment.

The methods, processes, and/or operations described herein may be performed by code or instructions to be executed by a computer, processor, controller, or other signal processing device. The code or instructions may be stored in a non-transitory computer-readable medium in accordance with one or more embodiments. Because the algorithms that form the basis of the methods (or operations of the computer, processor, controller, or other signal processing device) are described in detail, the code or instructions for implementing the operations of the method embodiments may transform the computer, processor, controller, or other signal processing device into a special-purpose processor for performing the methods herein.

The modules, models, managers, and other information processing, calculating, and computing features of the embodiments disclosed herein may be implemented in logic which, for example, may include hardware, software, or both. When implemented at least partially in hardware, the modules, models, managers, and other information processing, calculating, and computing features may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the modules, models, managers, and other information processing, calculating, and computing features may include, for example, a memory or other storage device for storing code or instructions to be executed, for example, by a computer, processor, microprocessor, controller, or other signal processing device. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods described herein.

It should be apparent from the foregoing description that various exemplary embodiments of the invention may be implemented in hardware. Furthermore, various exemplary embodiments may be implemented as instructions stored on a non-transitory machine-readable storage medium, such as a volatile or non-volatile memory, which may be read and executed by at least one processor to perform the operations described in detail herein. A non-transitory machine-readable storage medium may include any mechanism for storing information in a form readable by a machine, such as a personal or laptop computer, a server, or other computing device. Thus, a non-transitory machine-readable storage medium may include read-only memory (ROM), random-access memory (RAM), magnetic disk storage media, optical storage media, flash-memory devices, and similar storage media and excludes transitory signals.

It should be appreciated by those skilled in the art that any blocks and block diagrams herein represent conceptual views of illustrative circuitry embodying the principles of the invention. Implementation of particular blocks can vary while they can be implemented in the hardware or software domain without limiting the scope of the invention. Similarly, it will be appreciated that any flow charts, flow diagrams, state transition diagrams, pseudo code, and the like represent various processes which may be substantially represented in machine readable media and so executed by a computer or processor, whether or not such computer or processor is explicitly shown.

Accordingly, it is to be understood that the above description is intended to be illustrative and not restrictive. Many embodiments and applications other than the examples provided would be apparent upon reading the above description. The scope should be determined, not with reference to the above description or Abstract below but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

All terms used in the claims are intended to be given their broadest reasonable constructions and their ordinary meanings as understood by those knowledgeable in the technologies described herein unless an explicit indication to the contrary in made herein. In particular, use of the singular articles such as "a," "the," "said," etc. should be read to recite one or more of the indicated elements unless a claim recites an explicit limitation to the contrary.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

What is claimed is:

1. A method for generating an augmented training set of ultrasound images, comprising:
    randomly selecting one ultrasound image from a labeled set of ultrasound images;
    randomly selecting one of a set of ultrasound augmentation models, wherein the set of ultrasound augmentation models include at least one of comet tail artefacts model, near-field clutter model, range ambiguity model, beam-width artefact model, refraction model, aberration model, depth of focus of the ultrasound image alteration, gain alteration, quadrature bandpass (QBP) filter and weights alteration, and autoscan settings alteration;
    combining the randomly selected ultrasound image and randomly selected ultrasound augmentation model to produce an augmented ultrasound image, wherein combining the randomly selected ultrasound image and the randomly selected ultrasound augmentation model comprises a weight-based image blending comprising:

$$x = \varphi u + \omega r, \text{ where } \omega = 1 - \varphi$$

wherein u is a training case and r is an artefact model, and wherein a value for $\varphi$ and a value for $\omega$ is randomly selected based on the output of a pseudorandom number generator; and
    training a machine learning model using the augmented ultrasound image, wherein the machine learning model is a convolutional neural network model.

2. The method of claim 1, wherein combining the randomly selected ultrasound image and randomly selected ultrasound augmentation model includes using one of a weight-based image blending, Laplacian pyramid blending, selective, region-based blending, two-band blending, and graph-cuts based blending.

3. The method of claim 2, wherein a parameter of the blending is randomly chosen.

4. The method of claim 1, wherein the machine learning model performs one of the following tasks: classification; segmentation; detection; regression; data generation; view identification; and text generation.

5. The method of claim 1, wherein the ultrasound image is one of a color Doppler image, three-dimensional volumetric image, B-mode image, raw radiofrequency data image, pre-scan converted image, scan converted image, and elastography image.

6. The method of claim 1, wherein the one ultrasound image from a labeled set of ultrasound images is randomly selected based on the output of a pseudorandom number generator, and wherein the one of a set of ultrasound augmentation models is randomly selected based on the output of the pseudorandom number generator.

7. The method of claim 1, wherein randomly selecting one of a set of ultrasound augmentation models further comprises selecting a second one of the set of ultrasound augmentation models, and wherein combining the randomly selected ultrasound image and randomly selected ultrasound augmentation model to produce an augmented ultrasound image further comprises combining the randomly selected ultrasound image with both the first randomly selected ultrasound augmentation model and the second randomly selected ultrasound augmentation model to produce the augmented ultrasound image.

8. An ultrasound image augmentation training system, comprising:
- a machine learning model;
- an ultrasound image dataset including labeled ultrasound images;
- an augmentation controller configured to:
  - randomly select one of the labeled of ultrasound images from the ultrasound image dataset;
  - randomly select one of a set of ultrasound augmentation models, wherein the set of ultrasound augmentation models include at least one of comet tail artefacts model, near-field clutter model, range ambiguity model, beam-width artefact model, refraction model, aberration model, depth of focus of the ultrasound image alteration, gain alteration, quadrature bandpass (QBP) filter and weights alteration, and autoscan settings alteration; and
  - combine the randomly selected ultrasound image and randomly selected ultrasound augmentation model to produce an augmented ultrasound image, comprising a weight-based image blending comprising:

$x = \varphi u + \omega r$, where $\omega = 1 - \varphi$

- wherein u is a training case and r is an artefact model, and wherein a value for $\varphi$ and a value for $\omega$ is randomly selected based on the output of a pseudorandom number generator; and
- a training controller configured to train a machine learning model using the augmented ultrasound image.

9. The ultrasound image augmentation training system of claim 8, wherein combining the randomly selected ultrasound image and randomly selected ultrasound augmentation model includes using one of a weight-based image blending, Laplacian pyramid blending, selective, region-based blending, two-band blending, and graph-cuts based blending.

10. The ultrasound image augmentation training system of claim 9, wherein a parameter of the blending is randomly chosen.

11. The ultrasound image augmentation training system of claim 8, wherein the machine learning model is a neural network model.

12. The ultrasound image augmentation training system of claim 8, wherein the machine learning model performs one of the following tasks: multi-class classification; segmentation; detection; regression; and text generation.

13. The ultrasound image augmentation training system of claim 8, wherein the ultrasound image is one of a color Doppler image, three-dimensional volumetric image, B-mode image, raw radiofrequency data image, pre-scan converted image, scan converted image, and elastography image.

14. The ultrasound image augmentation training system of claim 8, wherein the one ultrasound image from a labeled set of ultrasound images is randomly selected based on the output of a pseudorandom number generator, and wherein the one of a set of ultrasound augmentation models is randomly selected based on the output of the pseudorandom number generator.

15. The ultrasound image augmentation training system of claim 8, wherein randomly selecting one of a set of ultrasound augmentation models further comprises selecting a second one of the set of ultrasound augmentation models, and wherein combining the randomly selected ultrasound image and randomly selected ultrasound augmentation model to produce an augmented ultrasound image further comprises combining the randomly selected ultrasound image with both the first randomly selected ultrasound augmentation model and the second randomly selected ultrasound augmentation model to produce the augmented ultrasound image.

* * * * *